United States Patent [19]

Brazdil, Jr. et al.

[11] Patent Number: 4,822,944

[45] Date of Patent: Apr. 18, 1989

[54] ENERGY EFFICIENT PROCESS FOR UPGRADING LIGHT HYDROCARBONS AND NOVEL OXIDATIVE COUPLING CATALYSTS

[75] Inventors: James F. Brazdil, Jr., Mayfield Village; John S. Hattenberger; Richard E. Hildebrand, both of Solon; Joseph P. Bartek, Highland Heights, all of Ohio

[73] Assignee: The Standard Oil Company, Cleveland, Ohio

[21] Appl. No.: 884,496

[22] Filed: Jul. 11, 1986

[51] Int. Cl.$^4$ .............................................. C07C 2/00
[52] U.S. Cl. .................................. 585/500; 585/310; 585/943
[58] Field of Search ................ 585/500, 943, 310, 643

[56] References Cited

U.S. PATENT DOCUMENTS

| | | | |
|---|---|---|---|
| 1,945,960 | 2/1934 | Winkler et al. | 260/170 |
| 1,986,238 | 1/1935 | Winkler et al. | 260/168 |
| 2,436,595 | 2/1948 | Nicholson et al. | 260/666 |
| 2,859,258 | 11/1958 | Fischer et al. | 260/683 |
| 2,885,455 | 5/1959 | Hennig | 585/643 |
| 3,244,765 | 4/1966 | Fouser | 260/679 |
| 4,120,910 | 10/1978 | Chu | 260/673 |
| 4,205,194 | 5/1980 | Mitchell | 585/500 X |
| 4,239,658 | 12/1980 | Mitchell | 585/500 X |
| 4,495,374 | 1/1985 | Jones et al. | 585/500 |
| 4,520,217 | 5/1985 | Minet | 585/415 |
| 4,523,049 | 6/1985 | Jones et al. | 585/500 |
| 4,533,780 | 8/1985 | Maffia | 585/330 |
| 4,547,607 | 10/1985 | Jones et al. | 585/500 |
| 4,560,821 | 12/1985 | Jones et al. | 585/500 |
| 4,567,307 | 1/1986 | Jones et al. | 585/500 |
| 4,608,449 | 8/1986 | Baerns et al. | 585/500 |

FOREIGN PATENT DOCUMENTS 0189079 7/1986 European Pat. Off. .
2148933 6/1986 United Kingdom .
2148935 6/1986 United Kingdom .

OTHER PUBLICATIONS

PCT International Application No. PCT/US86/01254.
J. Stocki and J. Glowinski, Pr. Nauk, Inst. Technol. Nieorg, Nawozow Miner. Politeth. Wroclaw, 24, 43 (1982); Chem. Abstr. 98, 162780e.
M. Reichert, Erdgas Rohst. Chem. Ind. Erzeng. Redaktionsgasen Huettenw., Symp. 1972 (Publ. 1973), pp. 6, 19; Chem. Abstr., 81, 65955g.
H. M. Smith et al., "Production of Motor Fuels from Natural Gas-I".
"Preliminary Report on the Pyrolysis of Methane", Report of Investigations, Department of Commerce-Bureau of Mines, R. I. 3143 (Oct., 1931).

Primary Examiner—William R. Dixon, Jr.
Assistant Examiner—James M. Hunter, Jr.
Attorney, Agent, or Firm—Raymond F. Keller; David J. Untener; Larry W. Evans

[57] ABSTRACT

A process for converting a gaseous reactant comprising methane or natural gas to higher molecular weight hydrocarbon products is disclosed which comprises: (1) contacting said gaseous reactant with an oxidative coupling catalyst at a reaction temperature of at least about 900° C. for an effective period of time to form an intermediate product comprising ethane, ethylene or a mixture thereof, said catalyst being characterized by a melting point above said reaction temperature; and (2) pyrolyzing said intermediate product at a temperature of at least about 900° C. for an effective period of time to form said higher molecular weight hydrocarbon products using exothermic heat generated by the formation of said intermediate product. Novel oxidative-coupling catalysts having melting points above about 900° C. are also disclosed.

3 Claims, 1 Drawing Sheet

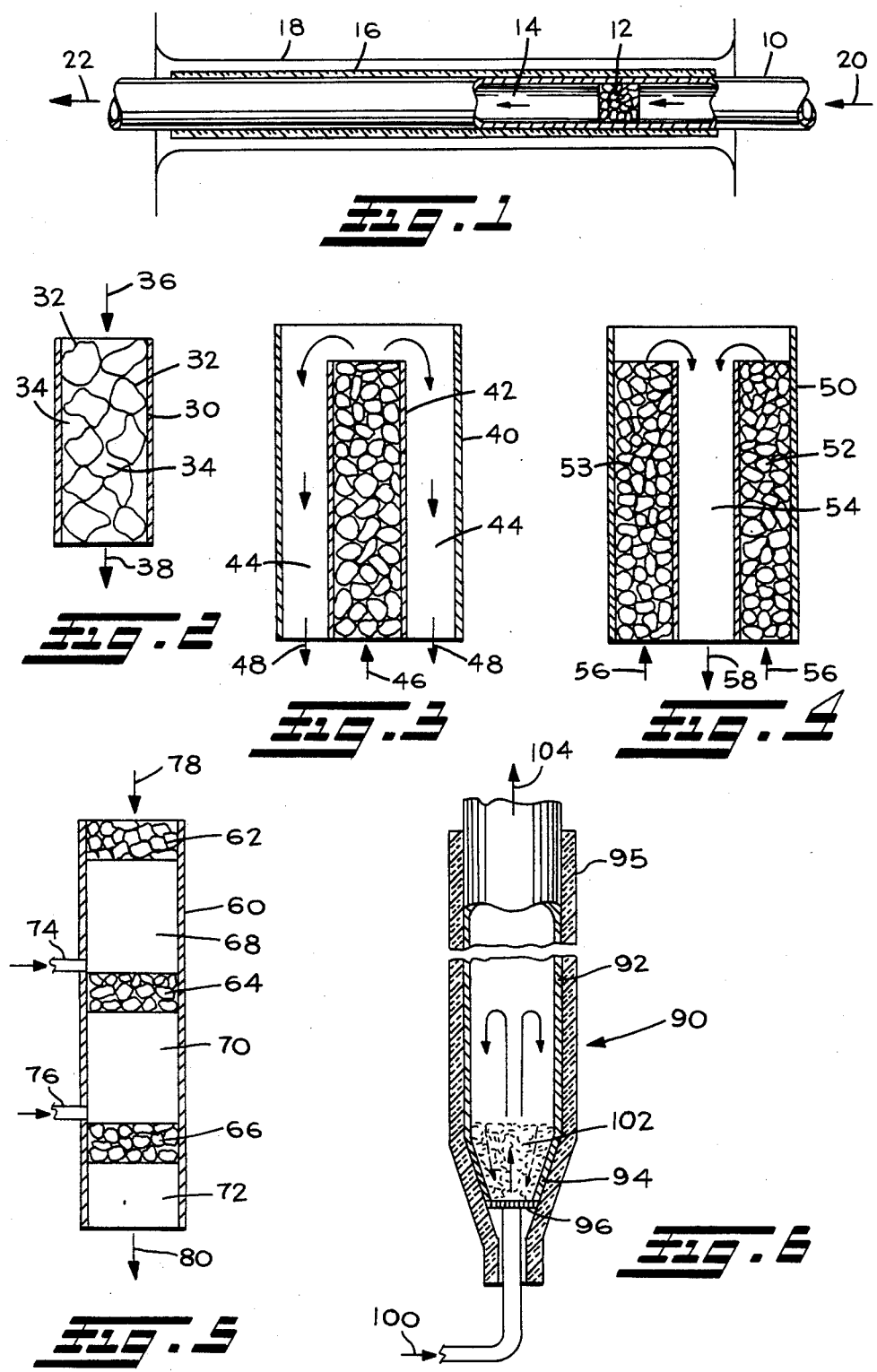

ENERGY EFFICIENT PROCESS FOR UPGRADING LIGHT HYDROCARBONS AND NOVEL OXIDATIVE COUPLING CATALYSTS

TECHNICAL FIELD

This invention relates to an energy efficient process for upgrading light hydrocarbons. More specifically, this invention relates to a process involving the use of both oxidative coupling and pyrolysis for converting methane or natural gas to higher molecular weight hydrocarbon products. This invention also relates to a novel oxidative coupling catalyst which is useful in the foregoing process.

BACKGROUND OF THE INVENTION

A major source of methane is natural gas. Natural gas at the wellhead typically contains about 40-95% methane depending on the particular source. Other constituents include about 10% ethane with the balance being made up of $CO_2$ and smaller amounts of propane, the butanes, the pentanes, nitrogen, etc.

Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, wellhead natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Natural gas is used principally as a source of heat in residential, commerical and industrial service.

Most processed natural gas is distributed through extensive pipeline distribution networks. As natural gas reserves in close proximity to gas usage decrease, new sources that are more distant require additional transportion. Many of these distant sources are not, however, amenable to transport by pipeline. For example, sources that are located in areas requiring economically unfeasible pipeline networks or in areas requiring transport across large bodies of water are not amenable to transport by pipeline. This problem has been addressed in several ways. One such solution has been to build a production facility at the site of the natural gas deposit to manufacture one specific product. This approach is limited as the natural gas can be used only for one product. preempting other feasible uses. Another approach has been to liquefy the natural gas using cryogenic techniques and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas at a temperature of about $-162°$ C., transporting the gas, and revaporizing it are complex and energy intensive.

Pyrolysis processes involving the conversion of methane to higher molecular weight hydrocarbons at high temperatures, in excess of about 1200° C., are known. These processes are, however, energy intensive and have not been developed to the point where high yields are obtained even with the use of catalysts. Some catalysts that are useful in these processes (e.g., chlorine) are corrosive under such operating conditions.

U.S. Pat. No. 4,507,517 and U.K. Patent Application GB 2 148 935A disclose catalytic processes for converting methane to $C_2^+$ hydrocarbons, particularly hydrocarbons rich in ethylene and/or benzene, at temperatures in excess of 1000° C. and high gas hourly space velocities greater than 3200 hr$^{-1}$. The process disclosed in the '517 patent uses a boron compound containing catalyst. The process disclosed in the U.K. application uses a catalyst containing a metal compound of the Group IA, IIA, IIIA, IVB or Actinide series metals.

Low temperature pyrolysis (e.g., to 250° C. and 500° C.) of hydrocarbon feedstocks to higher molecular weight hydrocarbons is described in U.S. Pat. Nos. 4,433,192; 4,497,970; and 4,513,164. The processes described in these patents utilize heterogeneous systems and solid acid catalysts. In addition to the solid acid catalysts, the reaction mixtures described in the '970 and '164 patents include oxidizing agents. Among the oxidizing agents disclosed are air, $O_2$–$O_3$ mixtures, S, Se, $SO_3$, $N_2O$, NO, $NO_3$, F, etc.

The catalytic oxidative coupling of methane at atmospheric pressure and temperatures of from about 500° C. to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysis*, 73, 9–19 (1982). This article discloses the use of single component oxide catalysts that exhibited methane conversion to higher. order hydrocarbons at rates no greater than 4%. The process by which Keller and Bhasin oxidized methane was cyclic, varying the feed composition between methane, nitrogen and air (oxygen) to obtain higher selectivities.

Methods for converting methane to higher molecular weight hydrocarbons at temperatures in the range of about 500° to about 1000° C. are also disclosed in U.S. Pat. Nos. 4,443,644; 4,443,645; 4,443,646; 4,443,647; 4,443,648; 4,443,649; and 4,523,049.

U.S. Pat. Nos. 4,172,810; 4,205,194; and 4,239,658 disclose the production of hydrocarbons including ethylene, ethane, propane, benzene and the like, in the presence of a catalyst-reagent composition which comprises: (1) a group VIII noble metal having an atomic number of 45 or greater, nickel, or a group Ib noble metal having an atomic number of 47 or greater; (2) a group VIb metal oxide which is capable of being reduced to a lower oxide; and (3) a group IIa metal selected from the group consisting of magnesium and strontium composited with a passivated, spinel-coated refractory support or calcium composited with a passivated, non-zinc containing spinel-coated refractory support. The feed streams used in the processes disclosed in these patents do not contain oxygen. Oxygen is avoided for the purposes of avoiding the formation of carbon oxides in the catalyst. Oxygen is generated for the reaction from the catalyst; thus periodic regenerations of the catalysts are required.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, a second metal selected from beryllium, magnesium, calcium, strontium, barium, and mixtures thereof, and optionally a promotor metal selected from copper, rhenium, tungsten, zirconium, rhodium, and mixtures thereof.

U.S. Pat. No. 4,560,821 discloses a continuous method for synthesizing hydrocarbons from a methane source which comprises contacting methane with particles comprising an oxidative synthesizing agent under synthesis conditions wherein particles recirculate between two physically separate zones: a methane contact zone and an oxygen contact zone. These particles are maintained in each of the two zones as fluidized beds of solids. The oxidative synthesizing agents are reducible oxides of metals selected from the group consisting of Mn, Sn, In, Ge, Pb, Sb and Bi.

PCT International Application No. PCT/GB85/00141 discloses a process for the production of synthesis gas and higher molecular weight hydrocarbons in which a saturated hydrocarbon and an oxygen containing gas having a ratio of hydrocarbon to oxygen of greater than the stoichiometric ratio for complete combustion are introduced into a bed of an inert particulate material, the upward flow rate of the hydrocarbon/oxygen containing gas stream being sufficient to fluidize or to produce a spouting action of the bed material, whereby at least a part of the particulate material is thrown up above the bed surface and subsequently falls back into the bed, the hydrocarbon and oxygen containing gas being ignited and reacted together, and the products of the reaction being withdrawn.

SUMMARY OF THE INVENTION

The present invention provides for a process for converting a gaseous reactant comprising methane or natural gas to higher molecular weight hydrocarbon products comprising: (1) contacting said gaseous reactant with an oxidative coupling catalyst at a reaction temperature of at least about 900° C. for an effective period of time to form an intermediate product comprising ethane, ethylene or a mixture thereof, said catalyst being characterized by a melting point above said reaction temperature; and (2) pyrolyzing said intermediate product at a temperature of at least about 900° C. for an effective period of time to form said higher molecular weight hydrocarbon products using exothermic heat generated by the formation of said intermediate product. The invention further provides for certain novel oxidative coupling catalysts having melting points above about 900° C. which are useful in the foregoing process.

BRIEF DESCRIPTION OF THE DRAWINGS

FIG. 1 is a partially cut-away view of a tubular reactor that is suitable for use in operating the process of the invention in a preferred manner.

FIG. 2 is a schematic illustration of a reactor that is suitable for use in operating the process of the invention in an alternative preferred manner.

FIG. 3 is a schematic illustration of a reactor that is suitable for use in operating the process of the invention in another alternative preferred manner.

FIG. 4 is a schematic illutration of a reactor that is suitable for use in operating the process of the invention in still another alternative preferred manner.

FIG. 5 is a schematic illustration of a reactor that is suitable for use in operating the process of the invention in still another alternative preferred manner.

FIG. 6 is a schematic illustration of a reactor that is suitable for use in operating the process of the invention in still another alternative preferred manner.

DESCRIPTION OF THE PREFERRED EMBODIMENT

The Oxidative Coupling Catalyst:

The conversion of the gaseous reactant to higher molecular weight hydrocarbons in accordance with the invention is accomplished using an oxidative coupling catalyst. Any oxidative coupling catalyst known in the art can be used, provided it has a melting point above the reaction temperature being employed. Preferably, the catalyst is a metal oxide other than a reducible metal oxide.

In a particularly advantageous embodiment of the invention the catalyst is selected from those metal oxide complexes having a melting point of at least about 900° C. that are represented by formula $$A_a D_b E_c O_x$$

wherein

A is an alkali metal, Ag, Tl or a mixture of two or more thereof,

D is Mn, Sn, Pb, Sb, Bi, Zn, a rare earth metal (including Sc, Y and La), an alkaline earth metal, or a mixture of two or more thereof, E is Ti, Zr, Hf, Nb, Ta, W, Al, Si, P, Ga, B, or a mixture of two or more thereof, a is a number in the range of zero to about 100, b is a number in the range of about 0.1 to about 100, c is a number in the range of zero to about 100, and x is the number of oxygens needed to fulfill the valence requirements of the other elements.

In a still more particularly advantageous embodiment of the invention the catalyst is selected from those metal oxide complexes having a melting point of at least about 900° C. that are represented by the formula $$G_a J_b L_c M_d O_x$$

wherein

G is Li, Ag, Cs, Rb, Tl or a mixture of two or more thereof,

J is Na, K, Mg, Ca, Sr, Ba, Zn, Ti, Zr, Hf, Sn, Sm, Eu, Yb, or a mixture of two or more thereof, L is La, Nd, Y, Sc or a mixture of two or more thereof, M is Al, Ga, B, P, Si, or a mixture of two or more thereof, a is a number in the range of zero to about 10, b is a number in the range of about 0.1 to about 10, c is a number in the range of about 0.1 to about 10, d is a number in the range of zero to about 100, and x is the number of oxygens needed to fulfill the valence requirements of the other elements.

In a still more advantageous embodiment of the invention the catalyst is a metal oxide complex represented by the formula $$SrLa_nO_x$$

wherein n is a number in the range of about 0.1 to about 100, preferably about 1 to about 20, more preferably about 10, and x is the number of oxygens needed to fulfill the valence requirements of the other elements.

The foregoing oxidative coupling catalysts can be formed in any conventional manner, such as tableting, pelleting, or supporting the metal oxide complex material on a carrier. The catalyst can be in the form of microspheroidal particles or monoliths. Suitable carrier materials include silica, alumina, fused alumina, zirconia, hafnia, titania, magnesia, germanium oxide, silicon carbide, clay, etc. In general, the carrier may be employed in amounts of up to about 99.5% by weight of the final catalyst composition.

The catalysts of the invention may be prepared by coprecipitation or by other methods known in the art. Generally they are prepared by mixing an aqueous solution of compounds containing the metal components, forming a precipitate and drying this precipitate. Examples of the compounds containing the metal components that are useful include but are not limited to oxides, hydroxides, inorganic salts (e.g., nitrates, phosphates, halides, carbonates, silicates, aluminates) and salts of organic acids (e.g., acetates, formates, butyrates, propionates, benzoates and the like). The catalyst may be calcined to produce desirable physical properties such as attrition resistance, optimum surface area and particle size.

The catalyst may be incorporated with the carrier by coating, impregnation or coprecipitation using known techniques. The catalyst can be coprecipitated with one carrier material (e.g., silica) and then the combination of catalyst and carrier can be coated on another carrier material (e.g., Alundum, a product of Norton Co. identified as fused alumina).

A particularly useful coating procedure is disclosed in U.S. Pat. No. 4,077,912, which is incorporated herein by reference. Briefly, this method involves partially wetting the carrier, contacting the partially wetted carrier with a powdered precipitate of the catalytic components, then gently agitating the mixture until the catalytic complex is formed. Agitation is conveniently conducted by placing the partially wetted carrier in a rotatiang drum and adding the powdered precipitate until none is taken up by the carrier. The liquid used to wet the carrier may include inorganic or organic liquids and is dependent upon the type of catalytic components employed. The liquid and the catalytic components should have a relatively high degree of attraction for each other.

The catalytic components can also be impregnated on the carrier by depositing a solution containing the catalytic components on the carrier using known techniques, then drying and calcining.

The catalytic components may optionally be individually coated or impregnated on a carrier using the above-indicated technique.

In order to further illustrate the preparation of the catalysts of the invention, the following example is provided. In the following example as well as throughout the specification and in the appended claims, all parts and percentages are by weight and all temperatures are in degrees centigrade, unless otherwise indicated.

EXAMPLE 1

$SrLa_{10}O_x$:

A slurry was prepared by mixing a solution of 179.9 grams of lanthanum nitrate hexahydrate in 200 grams of water and 2.3 grams of concentrated nitric acid, with 90 grams of ammonium carbonate in 500 grams of water. As the carbonate was added, the pH rose to 6.8 resulting in the formation of a precipitate. The mixture was stirred overnight and then filtered to remove the solids. The solids were dried overnight at 110° C. 33.5 grams of the dried solids were slurried in 205 grams of water. A solution of 30.0 grams of strontium nitrate in 51 grams of water was added to the slurry. The slurry was stirred and heated until it thickened. The thickened slurry was dried at 110° C. overnight resulting in the formation of a dry material. The dried material was heat treated for 19 hours at 290° C. and for 25 hours at 425° C. to provide the desired catalyst.

The Upgrading Process:

The gaseous reactants that are converted to higher molecular weight hydrocarbons in accordance with the process of the invention comprise methane or natural gas and may include additional hydrocarbons typically containing from 1 to about 5 carbon atoms. These hydrocarbons include, for example, ethane, ethylene, acetylene, propane, propylene, the butanes, the butylenes, the pentanes, the pentylenes, and the like, as well as mixtures of two or more of said hydrocarbons.

In a particularly advantageous embodiment of the invention, the gaseous reactant is natural gas. The natural gas that can be used can be either wellhead natural gas, as discussed above, or processed natural gas. The composition of processed natural gas varies with the needs of the ultimate user. A typical processed natural gas composition contains about 70% by weight methane, about 10% by weight ethane, about 10 to about 15% $CO_2$ and the balance being made up of smaller amounts of propane, butane and nitrogen.

The inventive process involves both oxidative coupling, which is an exothermic reaction, and pyrolysis, which is an endothermic reaction. Heat that is generated during the exothermic oxidative coupling reaction is used in the pyrolysis reaction. Ideally, once the reaction has started, the process can be operated without the addition of external heat. External heat may in some instances be needed to make up for heat loss through reactor walls, etc. An advantage of the invention, however, is that the amount of external heat, if any, that is required to effect the pyrolysis phase of the process is significantly less than with conventional pyrolysis processes.

The oxidative coupling step can be conducted in the presence or absence of oxygen in the feedstream. If oxygen is not provided in the feedstream, it must be generated by the catalyst. Preferably, however, oxygen is fed to the reactor with the gaseous reactant in the feedstream. Gaseous oxygen may be provided as substantially pure oxygen or diluted with nitrogen, carbon dioxide, carbon monoxide, or other inert gases (e.g., noble gases such as helium, neon, argon, etc.), or may be provided in the form of air. Preferably the feedstream contains from about 50% to about 90% by volume methane. The mole ratio of oxygen to methane preferably ranges from about 0.1 to about 1 mole of oxygen per mole of methane, more preferably from about 0.1 to about 0.5 mole of oxygen per mole of methane. The feedstream can contain from zero up to about 25 moles of nitrogen and/or other inert gases (e.g., noble gases such as helium, neon, argon, etc.), per mole of methane. The feedstream can also contain from zero up to about 25 moles of water per mole of methane.

The catalyst can be regenerated by passing oxygen over it at an elevated temperature. Preferably a mixture of oxygen and an inert gas (e.g., air) is passed over the catalyst at the reaction temperature for a sufficient period of time (e.g., 15 minutes) to reoxidize the catalyst. When oxygen or an oxygen source is provided in the feedstream, regeneration is not required or at least not required as often as with processes that do not employ oxygen in the feedstream.

The inventive process can be carried out by contacting the gaseous reactant with one of the catalysts described above in a fluid bed reactor, fixed bed reactor, spouted bed reactor or any other suitable reactor configuration such as a moving bed reactor, swing reactor system or membrane reactor. The reaction can be conducted in a continuous or a batchtype mode. The reaction temperature for both the oxidative-coupling step and pyrolysis step of the process is preferably at least about 900° C., more preferably in the range of about 900° C. to about 1500° C., more preferably from about 1000° C. to about 1400° C.

The average contact time of the gaseous reactants with the oxidative-coupling catalyst is preferably from about 1 millisecond to about 1000 milliseconds, more preferably from about 10 milliseconds to about 300 milliseconds.

The product of the oxidative coupling step is an intermediate product which comprises ethylene, ethane or a mixture thereof. This intermediate product may also comprise other higher molecular weight hydrocarbons (e.g., $C_3+$ hydrocarbons) as well as by-product water, carbon monoxide and carbon dioxide. Unconverted methane can be recycled through the catalyst so as to increase the overall yield of $C_2+$ hydrocarbons in the intermediate product.

Pyrolysis is effected by heating the intermediate product in an open or void space within a reactor at or near the reaction temperature being employed in the oxidative coupling step until the desired final products have been formed. This open or void space is sometimes hereinafter referred to as the pyrolysis zone. A critical feature of this invention relates to the ratio of the average residence time of the gases flowing through the pyrolysis zone, to the average contact time between the gaseous reactant and the catalyst. This ratio must be at least about 2:1, preferably at least about 5:1, more preferably at least about 10:1 and can be as high as 200:1 or higher. As a consequence, the ratio of the volume of the pyrolysis to the volume of the catalyst must also be at least about 2:1, preferably at least about 5:1, more preferably at least about 10:1, and can be as high as 200:1 or higher. The volume of the catalyst herein is the cumulative volume of all the catalyst particles employed in the reaction; this volume can be measured by conventional techniques (e.g., liquid displacement). The average residence time of the gases flowing through the pyrolysis zone is therefore preferably in the range of about 20 milliseconds up to about 200 seconds, more preferably about 20 milliseconds to about 100 seconds.

Preferably, the intermediate product and the catalyst are separated prior to pyrolysis. The separation can be relatively infinitesimal as, for example, in a loosely packed catalyst bed (see, for example, FIG. 2) wherein pyrolysis is effected in open or void spacings immediately adjacent the catalyst particles. The separation can also involve providing separate oxidative-coupling zones and pyrolysis zones within the same reactor (see, for example, FIGS. 1 and 3–6). The separation can also involve providing separate reactors, one for the oxidative-coupling step and one for the pyrolysis step.

The pressure for both the oxidative-coupling step and the pyrolysis step can range from atmospheric pressure up to about 40 atmospheres, preferably from atmospheric pressure up to about 4 atmospheres.

Achievement of the energy efficient potential of the process of the invention is dependent upon the design of the reactor(s) in which the oxidative coupling and pyrolysis steps are conducted. Preferably, a single reactor is used consisting of an enclosed insulated unit such as a tubular reactor wherein the oxidative-coupling zone and pyrolysis zone are in contact so that exothermic heat generated in the oxidative-coupling zone can be efficiently transferred by, for example, convection to the pyrolysis zone. An advantage of this invention is that since all or most of the heat required for the pyrolysis step of the reaction is generated within the oxidative-coupling zone during the oxidative-coupling reaction, the reactor need not be constructed with costly materials that have both high thermal stability and high thermal conductivity characteristics. This is in contrast to conventional pyrolysis reactors which are typically constructed of materials having such high thermal stability and high thermal conductivity characteristics due to the fact that the gaseous reactants must be heated up rapidly using external heat and the product mixture must be cooled down rapidly. Reactors that are suitable for use with the process of the invention can have various configurations, some of which are depicted in FIGS. 1–6.

In FIG. 1, tubular reactor 10 has an oxidative coupling zone 12 and a pyrolysis zone 14. The oxidative coupling zone contains the oxidative coupling catalyst which can be in any of the forms discussed above. The pyrolysis zone consists of an open or void space within the reactor 10. The ratio of the volume of the pyrolysis zone 14 to the volume of the catalyst within the oxidative coupling zone 12 must be, as discussed above, at least about 2:1, preferably at least about 5:1, more preferably at least about 10:1 and can be as high as 200:1 or higher. Tubular reactor 10 is enclosed within insulating jacket 16 and is heated by electric furnace 18. In operation, the feedstream 20 enters the tubular reactor 10, contacts the oxidative coupling catalyst in oxidative coupling zone 12 for an effective period of time to effect an oxidative coupling reaction and thereby form an intermediate product. The intermediate product advances through the pyrolysis zone 14 wherein a pyrolysis reaction is effected. Exothermic heat generated in the oxidative-coupling zone 12 is transferred, primarily by convection, to pyrolysis zone 14 to provide part or all (depending upon the effectiveness of insulation 16) of the heat necessary to effect the pyrolysis reaction in zone 14. Electric furnace 18 is provided primarily for initial start-up and to compensate for heat loss through the reactor walls, etc., during operation. The final product exits the tubular reactor 10 as effluent stream 22. The effluent stream can be cooled using conventional techniques or it can be further processed as discussed below.

FIGS. 2-5 illustrate alternative forms of the reactors in which the process of the invention can be performed. In each of these reactors the ratio of the volume of the open or void space to the volume of the catalyst particles must be at least about 2:1, preferably at least about 5:1, more preferably at least about 10:1, and as high as 200:1 or higher. In FIG. 2, the reactor consists of a fixed bed 30 which contains catalyst particles 32 and voids 34. The catalyst particles 32 are of sufficient size and geometry so as to provide the inclined ratios of catalyst volume to void space volume. In operation, the feedstream 36 enters the reactor bed 30, contacts catalyst particles 32 thereby undergoing oxidative coupling resulting in the formation of an intermediate product. The intermediate product then passes through voids 34 wherein pyrolysis occurs. The exothermic heat generated by the oxidative coupling reaction provides part or all of the heat necessary to effect the pyrolysis reaction. The final product exits the reactor as effluent stream 38.

In FIG. 3, a fixed bed reactor 40 includes a catalyst bed 42 and a pyrolysis zone 44 which consists of an open or void space. Feedstream 46 advances through catalyst bed 42 wherein oxidative coupling occurs resulting in the formation of an intermediate product. The intermediate product advances through open space 44 wherein pyrolysis occurs resulting in the formation of the final product. The final product exits the reactor as effluent stream 48. The exothermic heat generated in the oxidative coupling reaction provides part or all of the heat necessary for conducting the pyrolysis reaction.

In FIG. 4, a fixed bed reactor 50 includes catalyst beds 52 and 53 and a pyrolysis zone 54 which consists of an open or void space. Feedstream 56 advances through catalyst beds 52 and 53 wherein oxidative coupling occurs resulting in the formation of an intermediate product. The intermediate product advances through open space 54 wherein pyrolysis occurs resulting in the formation of the final product. The final product exits the reactor as effluent stream 58. The exothermic heat generated in the oxidative-coupling reaction provides part or all of the heat necesssary for conducting the pyrolysis reaction.

Referring to FIG. 5, a fixed bed reactor 60 houses catalyst beds 62, 64 and 66. Open spaces 68, 70 and 72 are provided downstream of catalyst beds 62, 64 and 66, respectively. Oxygen inlets 74 and 76 are provided in the sidewall of reactor 60 for admitting oxygen into catalyst beds 64 and 66, respectively. In operation, feedstream 78 enters the reactor 60 and passes sequentially through catalyst bed 62, open space 68, catalyst bed 64, open space 70, catalyst bed 66 and open space 72, and exits the reactor as effluent stream 80. In each of the catalyst beds 62, 64 and 66, an oxidative coupling reaction occurs, while in each of the open spaces 68, 70 and 72 a pyrolysis reaction occurs. Heat generated during the oxidative coupling reaction is transferred primarily by convection from the catalyst beds 62, 64 and 66 to the pyrolysis zones 68, 70 and 72, respectively, and provides part or all of the heat necessary for the pyrolysis reactions. Oxygen is introduced through inlets 74 and 76 to assist the oxidative coupling reactions in catalyst beds 64 and 66.

Referring to FIG. 6, fluidized bed reactor 90 includes a vertical column 92 and a conical section 94. Reactor 90 is enclosed within insulating jacket 95. Perforated plate 96 is positioned at the base of the conical section 94. Inlet tube 98 is provided at the bottom of conical section 94 for advancing the feedstream 100 upwardly into the reactor 90. A catalyst bed 102 is contained within conical section 94 on perforated plate 96. In operation, feedstream 100 is advanced upwardly through perforated plate 96 into catalyst bed 102 resulting in the fluidization of bed 102. The catalyst particles are projected upwardly into vertical column 92 by the flow of feedstream 100 and fall back into the bed by the force of gravity. The vertical extent of the column 92 and the flow of feedstream 100 are selected so as to limit or prohibit the escape of catalyst particles from the column 92. As the feedstream 100 passes through the catalyst bed 102, oxidative coupling occurs resulting in the formation of an intermediate product. The intermediate product advances upwardly through column 92 wherein pyrolysis occurs. The final product exits the column 92 as effluent stream 104. Exothermic heat generated during the oxidative coupling reaction advanced upwardly in column 92 from bed 102 by convection and provides part or all of the heat necessary for the pyrolysis reaction.

The composition of the higher molecular weight hydrocarbon products produced in accordance with the process of the invention is somewhat dependent upon the nature of the gaseous reactants that are initially used in the feedstream, and the conditions under which they are processed. Typically, the higher molecular weight hydrocarbon product will consist of hydrocarbons containing two or more carbon atoms. These hydrocarbon products generally consist of mixtures of both aliphatic and aromatic materials. Since the process of the present invention is wellsuited to a continuous, cyclic process, the lighter weight gaseous hydrocarbon products such as ethane or propane, etc., can be separated from the more desirable higher molecular weight hydrocarbon products (generally liquid) and recycled in the process for further conversion to even higher molecular weight hydrocarbon products. Methane is preferably recycled to the oxidation-coupling zone of the reactor while the $C_2+$ hydrocarbons are preferably recycled to the pyrolysis zone of the reactor. Unsaturated hydrocarbons present in the hydrocarbon products include ethylene and acetylene which may be recovered as products of the process or recycled to the pyrolysis zone for conversion to higher molecular weight products.

Preferred higher molecular weight hydrocarbon products made by the process of the present invention include aliphatic and/or aromatic products that are sufficiently liquid to be readily handleable and transportable in conventional pipeline systems. Included in this preferred group are hydrocarbons containing at least about 5 carbon atoms, more particularly, aromatic compounds containing at least 6 carbon atoms. The references in this application to "liquid hydrocarbons" is intended to include hydrocarbons that are substantially in the liquid form at a temperature of about 25° C. and a pressure of one atmosphere.

The higher molecular weight hydrocarbon products may be easily transported and have numerous applications in chemical processing as well as uses as fuels. For example, U.S. Pat. No. 4,100,218 discloses subjecting ethane to thermal cracking at temperatures of from about 815° C. to about 875° C. to produce an olefin-rich effluent which is then cooled to a temperature between about 315° C. and about 650° C. and contacted with a zeolite so as to produce a liquid hydrocarbon product suitable for use as LPG, gasoline and/or aromatics concentrate. U.S. Pat. No. 4,120,910 discloses converting ethane to liquid aromatic compounds with a process which comprises contacting, in the absence of added air or oxygen under conversion conditions, a gaseous paraffinic hydrocarbon feed containing ethane, with a catalyst comprising a crystalline aluminosilicate zeolite characterized by a constraint index within the approximate range of 1 to 12 and a silica to alumina ratio of at least 12, said catalyst having incorporated therein from about 0.01 to 30 weight percent based on the total weight of the catalyst of a metal or metal oxide wherein said metal is selected from the group consisting of Group VIII, IIB and IB metals and mixtures thereof whereby ethane present in said gaseous feed is converted to aromatic compounds and recovering said aromatic compounds as liquids. The foregoing patents are incorporated herein by reference. Other known processes are also available for the conversion of the higher molecular weight hydrocarbon products of the process of the invention to, for example, ethanol, ethylene glycol, polyethylene ethylene, and other additional chemicals useful as fuels, fuel additives and lubricants. Thus, the process of the invention may be integrated with another process for converting the higher molecular hydrocarbon products to useful chemicals.

In order to further illustrate the process of the invention, the following Example 2 is provided.

EXAMPLE 2

The oxidation of methane over the catalyst of Example 1 was carried out by passing a methane/oxygen/nitrogen mixture over a bed of the catalyst in a heated quartz tube with an axial quartz thermowell passing through the bed. The reactor tube had an external diameter of 12 mm and an internal diameter of 8 mm. The external diameter of the thermowell was 3 mm. The annulus occupied by the catalyst was 2.5 mm thick. The catalyst bed was placed near the top of the heated zone of a 1" diameter×12" long laboratory furnace. Gases were mixed and fed down from the top of the reactor tube. The first part of the heated portion of the reactor tube was filled with quartz chips to provide preheat. The portion of the reactor below the catalyst was left empty except for a portion of the thermowell extending to the furnace center. The ratio of the void space for the pyrolysis zone to the catalyst volume was 15. The thermocouple at the center of the reactor read 10°–20° C. higher than the furnace controller in the absence of reaction. The furnace control thermocouple was placed in a well through the side of the furnace such that only a short section was in the hot zone, accounting for this difference. The reaction temperature rose during operation because of the exothermic oxidative coupling reaction. The difference between the maximum temperature and the temperature in the absence of reaction (the "exotherm") varied with the activity of the catalyst and the amount of oxygen in the feedstream.

Prior to commencing operation, the catalyst was heat treated in the reactor in an oxygen/nitrogen stream. Water picked up during storage of the catalyst was removed by heating it to 300° C. The catalyst was then heated to 700° C. gradually over a few hours and held there for two hours.

Methane, ethane, ethylene, propylene, propane, butanes and butylenes were separated on a ten foot long gas chromatographic column and quantified with a flame ionization detector. Relative molar responses, according to Dietz, were used to obtain the ratio of hydrocarbon products to methane from the flame detector peak area. These responses are close to the unit response per carbon atom rule (1.07/1.96/2.0 areas for an equimolar mixture of $CH_4/C_2H_4/C_2H_6$) which applies for this type of detector. The response was checked for members of the series using standard gas mixtures. Oxygen, nitrogen, methane, carbon monoxide and carbon dioxide were determined with a gas chromatograph with a thermal conductivity detector; the lighter gases were separated by a molecular seive column arranged in parallel with a column which separated $CO_2$ from the light gases and the $C_2$ and higher hydrocarbons. Methane conversion was determined by comparison of feed and product gas analyses from this chromatograph. Higher hydrocarbon products in the liquid range, especially aromatics such as benzene and toluene, were found by analyzing the product vapor stream with a gas chromatograph equipped with a polar capillary column and a flame ionization detector.

The results are indicated in the following Table. In the test runs tabulated in this table, the ratio of methane to oxygen to nitrogen in the feedstream on a volume basis was 1.00:0.14:0.29. The feed rate was 220 cc./min. The weight of the catalyst was 0.56 gram. The catalyst had a volume of 0.5 cc. The average contact time with the catalyst was 30 milliseconds. The methane that was used was "C.P." Grade, that is, over 99.5% pure. A small amount of ethane, 0.4 mole % or less, was found in the methane fed. This would correspond to an added yield of 0.8% maximum, if it were included with the products. In the material balance it is considered to pass through unreacted, and thus subtracted from the products before the yield is calculated.

TABLE

| Run No. | Furnace Temp. °C. | Catalyst Temp. °C. | Pyrolysis Temp. °C. | Methane Conversion (%) | $C_2+$ Hydrocarbon (%)* | Ethylene + Acetylene (%)* | $C_2$ unsat/ $C_2$ sat** | Aromatics (%)*** | CO (%)* | $CO_2$ (%)* | $H_2/CO/CO_2$ (%)**** |
|---|---|---|---|---|---|---|---|---|---|---|---|
| 1 | 900 | 915 | 915 | 14.20 | 8.70 | 6.55 | 6.88 | 0.20 | 0.85 | 4.87 | 4.3/0.65/3.74 |
| 2 | 900 | 916 | 920 | 14.55 | 9.14 | 7.04 | 7.09 | 0.21 | 0.89 | 4.52 | 4.1/0.69/3.49 |
| 3 | 950 | 959 | 971 | 14.36 | 8.24 | 6.25 | 20.30 | 0.70 | 1.43 | 4.70 | 5.7/1.08/3.56 |
| 4 | 975 | 979 | 997 | 14.28 | 7.79 | 5.615 | 24.70 | 1.09 | 1.91 | 4.57 | 6.6/1.43/3.43 |
| 5 | 1000 | 993 | 1014 | 15.20 | 7.53 | 4.93 | 24.48 | 1.60 | 2.65 | 5.03 | 8.0/1.96/3.71 |
| 6 | 1030 | 1007 | 1041 | 16.02 | 7.85 | 4.52 | 24.76 | 2.57 | 3.29 | 4.89 | 9.6/2.39/3.56 |
| 7 | 1080 | 1044 | 1084 | 19.11 | 8.39 | 4.95 | 32.00 | 2.80 | 6.41 | 4.32 | 15.2/4.37/2.48 |

*Percent methane in feedstream converted to indicated hydrocarbon or carbon oxide
**Ratio of moles of ethylene + acetylene divided by moles of ethane in effluent stream
***Percent methane in feedstream converted to aromatics (predominantly benzene, toluene, xylene and naphthalene)
****Volume percentage based on volume of effluent stream While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A process for converting a gaseous reactant comprising methane or natural gas to higher molecular weight hydrocarbon products comprising:
   (1) contacting said gaseous reactant with an oxidative coupling catalyst at a reaction temperature of at least about 900° C. for an effective period of time to form an intermediate product comprising ethane, ethylene or a mixture thereof, said catalyst being characterized by a melting point above said reaction temperature and being represented by the formula $$SrLa_nO_x$$

wherein n is a number in the range of about 0.1 to about 100, and x is the number of oxygens needed to fulfill the valence requirements of the other elements; and
   (2) pyrolyzing said intermediate product at a temperature of at least about 900° C. for an effective period of time to form said higher molecular weight hydrocarbon products using exothermic heat generated by the formation of said intermediate product.

2. The process of claim 1 wherein n is in the range of about 1 to about 20.

3. The process of claim 1 wherein n is about 10.

* * * * *